United States Patent
Nishida et al.

(10) Patent No.: US 11,844,850 B2
(45) Date of Patent: Dec. 19, 2023

(54) WATER IN OIL TYPE COSMETIC COMPOSITION FOR PREVENTING SYNERESIS

(71) Applicant: SHISEIDO COMPANY, LTD., Tokyo (JP)

(72) Inventors: Keita Nishida, Kanagawa (JP); Saki Kamada, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/976,993

(22) PCT Filed: Mar. 1, 2019

(86) PCT No.: PCT/JP2019/008024
§ 371 (c)(1),
(2) Date: Aug. 31, 2020

(87) PCT Pub. No.: WO2019/172107
PCT Pub. Date: Sep. 12, 2019

(65) Prior Publication Data
US 2021/0000706 A1   Jan. 7, 2021

(30) Foreign Application Priority Data

Mar. 8, 2018 (JP) ................................ 2018-042197

(51) Int. Cl.
| | | |
|---|---|---|
| *A61Q 19/00* | (2006.01) | |
| *A61Q 1/00* | (2006.01) | |
| *A61K 8/06* | (2006.01) | |
| *A61K 8/00* | (2006.01) | |
| *A61K 8/04* | (2006.01) | |
| *A61K 8/25* | (2006.01) | |
| *A61K 8/46* | (2006.01) | |
| *A61K 8/81* | (2006.01) | |

(52) U.S. Cl.
CPC .............. *A61K 8/064* (2013.01); *A61K 8/042* (2013.01); *A61K 8/25* (2013.01); *A61K 8/466* (2013.01); *A61K 8/8182* (2013.01); *A61Q 19/00* (2013.01); *A61K 2800/612* (2013.01)

(58) Field of Classification Search
CPC .......... A61Q 19/00; A61Q 17/04; A61Q 1/02; A61Q 1/00; A61Q 5/00; A61Q 19/08; A61K 2300/00; A61K 2800/10; A61K 8/064; A61K 9/0014; A61K 2800/48; A61K 8/06; A61K 8/022; A61K 8/585; A61K 8/92; A61K 8/044; A61K 2800/52
See application file for complete search history.

(56) References Cited

U.S. PATENT DOCUMENTS

| | | | | |
|---|---|---|---|---|
| 5,036,108 A | * | 7/1991 | Asahi ..................... | A61K 8/894 514/772 |
| 5,196,187 A | * | 3/1993 | Nicoll .................... | A61K 8/585 424/59 |
| 2003/0118619 A1 | | 6/2003 | Suares et al. | |
| 2003/0152598 A1 | | 8/2003 | Heidenfelder et al. | |
| 2004/0037797 A1 | * | 2/2004 | Nielsen .................. | A61K 8/064 424/70.15 |
| 2005/0002973 A1 | * | 1/2005 | Johansson ................ | A61K 8/86 424/401 |
| 2009/0017081 A1 | | 1/2009 | Takakura et al. | |
| 2009/0041817 A1 | * | 2/2009 | Takakura ............. | A61K 8/4946 424/59 |
| 2010/0008875 A1 | | 1/2010 | Oguchi et al. | |
| 2010/0291011 A1 | | 11/2010 | Ikebe et al. | |
| 2012/0288458 A1 | | 11/2012 | Yamaguchi et al. | |
| 2013/0344013 A1 | | 12/2013 | Ikebe et al. | |
| 2014/0017191 A1 | * | 1/2014 | Ibe ........................ | A61Q 19/00 424/78.02 |
| 2014/0135406 A1 | * | 5/2014 | Lee ......................... | A61K 8/20 514/772.3 |

(Continued)

FOREIGN PATENT DOCUMENTS

| | | | | |
|---|---|---|---|---|
| CN | 1406577 A | 4/2003 | | |
| CN | 102791249 | 11/2012 | | |
| CN | 105267051 A | 1/2016 | | |
| EP | 2997956 B1 | * | 4/2017 | ........... A61K 8/0241 |
| JP | 2007-182391 A | 7/2007 | | |
| JP | 2007-217379 A | 8/2007 | | |
| JP | 2008-7444 A | 1/2008 | | |
| JP | 2008-208052 A | 9/2008 | | |
| JP | 2010-100553 A | 5/2010 | | |
| JP | 2010-248118 A | 11/2010 | | |

(Continued)

OTHER PUBLICATIONS

International Search Report (ISR) dated Jun. 4, 2019 file in PCT/JP2019/008024 and its Partial English translation.

(Continued)

*Primary Examiner* — Tracy Liu
(74) *Attorney, Agent, or Firm* — Rankin, Hill & Clark LLP

(57) ABSTRACT

The present disclosure provides a water in oil type cosmetic composition that prevents syneresis and exhibits favorable stability. A water in oil type cosmetic composition for preventing syneresis of the present disclosure is characterized by containing a compound which is solubilized by being neutralized as an active component. In addition, a preferred embodiment of the water in oil type cosmetic composition for preventing syneresis of the present disclosure is characterized by the compound which is solubilized by being neutralized being a water soluble compound which has a sulfonic acid group. Further, a water in oil type cosmetic of the present disclosure is characterized by containing: a compound which is solubilized by being neutralized; a gelling agent; water; and a powder component; the viscosity of the water in oil cosmetic being greater than or equal to 7000 mPa·s.

6 Claims, No Drawings

(56) References Cited

U.S. PATENT DOCUMENTS

2014/0148516 A1* 5/2014 Sasaki .................. A61K 8/92
514/785

FOREIGN PATENT DOCUMENTS

| JP | 2011-68583 A | 4/2011 |
|----|--------------|--------|
| JP | 2011-153079 A | 8/2011 |
| JP | 2011-256292 A | 12/2011 |
| WO | 02/051377 A1 | 7/2002 |
| WO | 2009/104353 A1 | 8/2009 |
| WO | 2013/031510 A1 | 3/2013 |

OTHER PUBLICATIONS

Written Opinion of the International Searching Authority (Written Opinion of the ISA) dated Jun. 4, 2019 file in PCT/JP2019/008024 and its Partial English translation.

Japanese Office Action dated Nov. 24, 2021 for corresponding Japanese Patent Application No. 2018-042197 and its English translation.

Partial European Search Report (ESR) dated Jul. 28, 2022 for European Patent Application No. 19764026.1.

"Water Pact SPF 50+ PA+++", Database GNPD (Online), Mintel, 2016, total 6 pages; Cited in ESR.

"Cushion Foundation SPF 50", Database GNPD (Online), Mintel, 2018, total 4 pages; Cited in ESR.

"Cushion SPF 35 PA++", Database GNPD (Online), Mintel, 2018, total 12 pages; Cited in ESR.

Extended European Search Report (EESR) dated Dec. 7, 2022 for European Patent Application No. 19764026.1.

"Heartbeats Hydrated Lustrous Lip Tint", Mintel, 2018, pp. 1-4; Cited in EESR.

"CC Cream SPF35/PA++", Mintel, 2017, pp. 1-6; Cited in EESR.

"Solar Kids Sunscreen SPF50", Mintel, 2012, pp. 1-3; Cited in EESR.

Chinese Office Action (CNOA) dated Sep. 21, 2022 issued in Chinese application No. 201980017241.8 and its partial English translation.

Chinese Office Action (CNOA) dated Apr. 13, 2023 for Chinese Patent Application No. 201980017241.8.

* cited by examiner

WATER IN OIL TYPE COSMETIC COMPOSITION FOR PREVENTING SYNERESIS

CROSS REFERENCE TO RELATED APPLICATIONS

The present application is a National Phase Entry of International Patent Application No. PCT/JP2019/008024 filed on Mar. 1, 2019, which claims priority under 35 U.S.C. § 119(a) to Japanese Patent Application No. 2018-042197 filed on Mar. 8, 2018. Each of the above applications is hereby expressly incorporated by reference, in its entirety, into the present application.

TECHNICAL FIELD

The present disclosure is related to a water in oil type cosmetic composition for preventing syneresis and a water in, oil type cosmetic.

BACKGROUND ART

Presently, various cosmetic compositions that include an oil in water type and a water in oil type are widely being utilized. For example, as cosmetic compositions with the purpose of preventing sunburn, ultraviolet ray absorbing agents or ultraviolet ray scattering agents (zinc oxide, titanium dioxide, etc.) are blended into such cosmetics in order to block UV irradiation of the skin and to obtain a high SPF (Sun Protection Factor) value. Because a refreshing sensation of use is desired of cosmetics including such sunscreen cosmetics, oil in water (hereinafter, also referred to as O/W) type cosmetics are increasing. On the other hand, the water in oil (hereinafter, also referred to as W/O) type creams are preferred for a base cosmetic, foundation, etc., from the viewpoints of utilization methods and covering performance.

However, in W/O type creams, there is a high risk of syneresis (oil separation) over time, and the preventive measures therefor have not been completely clarified.

For example, a water-in-oil type emulsified cosmetic composition which has superior makeup lasting qualities and emulsion stability, and also has extremely superior stability that does not cause an outer oil phase to seep out, particularly even in a tube container or the like is known (Japanese Unexamined Patent Publication No. 2007-182391). This water in oil type emulsified cosmetic composition contains (A) from 0.5 to 10% by mass of alkyl modified silicone, (B) from 0.1 to 10% by mass of cross-linked organopolysiloxane polymer, (C) from 0.1 to 10% by mass of dimethiconol, (D) 1 to 20% by mass of polyvalent alcohol, and (E) from 5.0 to 60.0% by mass of water.

In Japanese Unexamined Patent Publication No. 2007-182391, blending of an organically modified clay mineral or hydrophobized silica is a common and effective method because it enables gelling regardless of the type and properties of an oil phase, and increased viscosity and stabilization are possible. However, in this method, the formation of gel structures may be gradually completed depending on conditions, and the aforementioned syneresis phenomenon occurs over a long period of time, and seepage of oil may occur several months or one year after the end of an accelerated test period. Therefore, the technique of Japanese Unexamined Patent Publication No. 2007-182391 is that which attempts to solve the problem of the outer oil phase seeping phenomenon by utilizing an alkyl modified silicone or the like without using an organically modified clay mineral.

However, in water in oil type compositions, although the mechanism of syneresis has been studied for many years, the main cause remains unknown. It is desirable for phenomena such as syneresis to be resolved. Syneresis is caused by, for example, only an oil component and the like flowing out from a composition in which an upper layer is oil and a lower layer is powder and emulsified particles. When utilized, such compositions are shaken to be utilized. Syneresis occurs in some compositions immediately, and may take several days in some other compositions. In many cases, there is a possibility that the problem of syneresis is caused by the inclusion of different substances such as water, oils, and powders. Therefore, it is desirable to be able to obtain a composition in a single layer, but such compositions have not been known to date. In addition, the use of a gelling agent has many advantages such as imparting a refreshing sensation of use. Therefore, a cosmetic that prevents syneresis and the like and exhibits favorable stability even if a gelling agent is utilized is desirable, if possible.

However, no conventional composition for a cosmetic, no cosmetic, etc. that prevents syneresis, etc. and exhibits favorable stability heretofore exists, including the composition which is disclosed in Japanese Unexamined Patent Publication No. 2007-182391.

The present disclosure has been developed in view of the foregoing circumstances. The present disclosure provides a water in oil type cosmetic composition, etc. that prevents syneresis and exhibits favorable stability.

In order to achieve the aforementioned object, the present inventors have conducted diligent research on the phenomenon of syneresis in cases that various gelling agents are utilized, and have discovered a water in oil type cosmetic composition for preventing syneresis according to the present disclosure.

That is, the water in oil type cosmetic composition for preventing syneresis of the present disclosure is characterized by containing a compound which is solubilized by being neutralized as an active component.

In addition, a preferred embodiment of the water in oil type cosmetic composition for preventing syneresis of the present disclosure is characterized by the compound which is solubilized by being neutralized being a water soluble compound which has a sulfonic acid group.

Further, a water in oil type cosmetic of the present disclosure is characterized by containing: a compound which is solubilized by being neutralized; a gelling agent; water; and a powder component; the viscosity of the water in oil cosmetic being greater than or equal to 7000 mPa·s.

Still further, a preferred embodiment of the water in oil type cosmetic of the present disclosure is characterized by the mass ratio of the compound which is solubilized by being neutralized with respect to water being greater than or equal to 0.02.

In addition, a preferred embodiment of the water in oil type cosmetic of the present disclosure is characterized by the mass ratio of the gelling agent with respect to the powder component being less than or equal to 0.1.

Further, a preferred embodiment of the water in oil type cosmetic of the present disclosure is characterized by the gelling agent being a clay mineral.

Still further, a preferred embodiment of the water in oil type cosmetic of the present disclosure is characterized by the clay mineral being an organically modified clay mineral.

In addition, a preferred embodiment of the water in oil type cosmetic of the present disclosure is characterized by the compound which is solubilized by being neutralized is a water soluble compound which has a sulfonic acid group.

Further, a preferred embodiment of the water in oil type cosmetic of the present disclosure is characterized by further containing an emulsifying agent.

Advantageous Effects of the Disclosure

According to the water in oil type cosmetic composition for preventing syneresis and the water in oil type cosmetic of the present disclosure, an advantageous effect that oil flowing out first when the composition and the cosmetic is utilized from within a container, resulting in an unpleasant sensation of use can be prevented is exhibited.

DESCRIPTION OF EMBODIMENTS

The water in oil type cosmetic composition for preventing syneresis of the present disclosure is characterized by containing a compound which is solubilized by being neutralized as an active component. In the present disclosure, the compound which is solubilized by being neutralized is not particularly limited as long as it is capable of preventing syneresis of the water in oil type cosmetic composition. This is based on the finding by the present inventors that a compound which is solubilized by being neutralized, and particularly a water soluble compound which has a sulfonic acid group, was capable of preventing syneresis of a W/O cream during the course of consideration of a series of sun care products, in which syneresis occurs in W/O creams, and research regrading how to solve the syneresis phenomenon.

In the present disclosure, it is only necessary for the amount of the compound which is solubilized by being neutralized to be an effective amount to prevent syneresis of the water in oil type cosmetic composition, and the amount may be set as appropriate.

In addition, in a preferred embodiment of the water in oil type cosmetic composition of the present disclosure, the compound which is solubilized by being neutralized may contain a compound which has a sulfonic acid group. Examples of compounds which have a sulfonic acid group may be at least one selected from among a group consisting of phenyl benzimidazole sulfonic acid, terephthalylidene dicanful sulfonic acid, and an (acryloyl dimethyl taurine ammonium/VP) copolymer. In the present disclosure, examples of the compound which has a sulfonic acid group may be phenyl benzimidazole sulfonic acid and terephthalylidene dicanful sulfonic acid. From the viewpoint of the water in oil type cosmetic composition of the present disclosure being in the form of a cream, the effect of preventing syneresis can be particularly exhibited in the case that the viscosity of the composition is greater than or equal to 7000 mPa·s. In the present disclosure, the following measuring device and measuring conditions may be employed to measure the viscosity of the composition or the cosmetic.

Measuring Device: Shibaura System Co., Ltd. B type Viscometer Model Number VDA2

Measurement conditions: 12 rpm, 1 minute, 30° C.

Further, the water in oil type cosmetic of the present disclosure is characterized by containing: a compound which is solubilized by being neutralized; a gelling agent; water; and a powder component; the viscosity of the water in oil cosmetic being greater than or equal to 7000 mPa·s.

In the present disclosure, the compound which is solubilized by being neutralized is not particularly limited. However, a water soluble compound which has a sulfonic acid group is a preferable type of compound from the viewpoint of preventing syneresis. Examples of water soluble compounds which have such a sulfonic acid group include phenyl benzimidazole sulfonic acid, terephthalylidene dicanfur sulfonic acid, (acryloyl dimethyl taurine ammonium/VP) copolymer, etc. It is preferable for the water soluble compound which has a sulfonic acid group to be at least one selected from the group consisting of phenyl benzimidazole sulfonic acid, terephthalylidene dicanfur sulfonic acid, and (acryloyl dimethyl taurine ammonium/VP) copolymer. These compounds may be employed alone or in combinations of two or more types.

The compound which has a sulfonic acid group may be blended in an amount within a range from 0.01 to 5% by mass, and more preferably a range from 0.1 to 3% by mass, based on the total amount of the water in oil cosmetic from the viewpoint of preventing syneresis. This range is set because if the content of the compound is less than 0.01% by mass, there is a possibility that no effect will be exhibited, and if the content of the compound is greater than 5% by mass, there is a possibility that precipitation and crystallization will occur.

In the present disclosure, particularly in the case that the compound which is solubilized by being neutralized is a water soluble UV absorbing agent, the water in oil type cosmetic composition of the present disclosure can be used as a sunscreen cosmetic composition. In this case, it is more preferable for the content of the water soluble compound to be an amount of 0.1 to 5% by mass, in order to be able to absorb ultraviolet rays within a wider range. In the case that the content of the water soluble compound is less than 0.1% by mass, the effect of preventing absorption of ultraviolet rays by the skin is not sufficiently exhibited, and if the content of the water soluble compound is greater than 5% by mass, stickiness may occur, or the water soluble compound may not be completely dissolved and crystals may precipitate, which is not preferable.

In addition, the gelling agent is not particularly limited in the present disclosure. Examples of the gelling agent include oil based gelling agents such as dextrin fatty acid ester, sucrose fatty acid ester, organically modified clay mineral, 12-hydroxystearic acid and metal soap. In the present disclosure, examples of the gelling agent include clay minerals and further organically modified clay minerals from the viewpoint of obtaining a thickening effect with a small amount of the gelling agent. Examples of the organically modified clay mineral include disteardimonium hectorite, dimethyl alkyl ammonium hectorite, benzyl dimethyl stearyl ammonium hectorite, distearyl dimethyl ammonium chloride treated aluminum magnesium silicate, etc. As commercially available products, Benton 27 (benzyl dimethyl stearyl ammonium chloride treated hectorite, produced by National Red) and Benton 38 (distearyl dimethyl ammonium chloride treated hectorite, produced National Red) may be favorably utilized.

In the present disclosure, clay minerals that include these organically modified clay minerals may be blended in an amount within a range from 0.01 to 2.0% by mass, and more preferably within a range from 0.5 to 2.0% by mass, based on the total amount of the water in oil cosmetic. If the content of the clay mineral is less than 0.01% by mass, it is difficult to obtain sufficient stability, and a content of the clay mineral up to 2.0% by mass imparts a refreshing sensation of use. Blending more of the clay mineral is not preferable from the viewpoint of usability, as take up properties with fingers will deteriorate. In addition, spreading properties on skin will become heavy and deteriorate.

The powder component is not particularly limited as long as it is that which is capable of being employed in a water in oil emulsion type cosmetic. Examples of the powder components include inorganic powders such as talc, mica, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, tungstate metal salt, magnesium, spherical silica, zeolite, barium sulfate, calcined calcium sulfate (calcined gypsum), calcium phosphate, fluoroapatite, hydroxyapatite, ceramic powder, metallic soap (zinc myristate, calcium palmitate, aluminum stearate, etc.), and boron nitride; spherical organic powders such as polyamide spherical resin powder (nylon spherical powder), spherical polyethylene, cross-linked poly (meth) acrylate methyl spherical resin powder, spherical polyester, cross linked polystyrene spherical resin powder, styrene acrylate copolymer spherical resin powder, benzoguanamine spherical resin powder, polytetrafluoroethylene spherical powder, and spherical cellulose; inorganic white pigments such as zinc oxide, titanium oxide, barium sulfate, zinc oxide coated or complexed with silicate anhydride; inorganic red pigments such as iron oxide (red iron oxide) and iron titanate; inorganic brown pigments such as γ-iron oxide; inorganic yellow pigments such as yellow iron oxide and loess; inorganic black pigments such as black iron oxide, carbon black, and low order titanium oxide; inorganic purple pigments such as mango violet and cobalt violet; inorganic green pigments such as chromium oxide, chromium hydroxide, and cobalt titanate; inorganic blue pigments such as ultramarine blue and navy blue; mica titanium, red iron oxide coated mica, red iron oxide coated mica titanium, carmine coated mica titanium, titanium blue oxide coated mica titanium, titanium oxide coated synthetic phlogopite, red iron oxide/titanium oxide coated synthetic phlogopite, titanium oxide coated glass flakes, red iron oxide/titanium oxide coated glass flakes, titanium oxide coated alumina flakes, titanium oxide coated silica flakes, iron oxide/silica coated aluminum, iron oxide/silica coated iron oxide, metal coated plate shaped powder, polyethylene terephthalate/polymethyl methacrylate laminated film powder (may contain a coloring material), polyethylene terephthalate/polyolefin laminated film powder (may contain a coloring material), epoxy resin coated aluminum vapor deposited polyethylene terephthalate (may contain a coloring material), aluminum vapor deposited polyethylene terephthalate (may contain a coloring material)), urethane resin coated aluminum vapor deposited polyethylene terephthalate (may contain a coloring material), acrylic resin coated aluminum powder (may contain a coloring material), titanium oxide coated mica, titanium oxide coated bismuth oxychloride, titanium oxide coated talc, titanium oxide coated colored mica, bismuth oxychloride, pearl agents, and lame agents such as fish scale foil. Among these powders, titanium oxide, zinc oxide, talc, polymethyl silsesquioxane, methyl methacrylate cross polymer, iron oxide, and spherical polyalkyl acrylate are preferable. These powders may be employed alone or in combinations of two or more types as appropriate.

These powder components may be blended in an amount within a range from 1 to 40% by mass with respect to the total amount of the water in oil type cosmetic, from the viewpoint of usability. This range is set because of the content of the powder component is less than 1% by mass, there is a possibility that the cosmetic will become sticky and usability will deteriorate. Conversely, if the content of the powder component is greater than 40% by mass, there is a possibility that usability will deteriorate by the spreading properties of the cosmetic becoming poor and a refreshing sensation of use not being imparted.

Note that both hydrophilic and hydrophobic powder components are listed above. From the viewpoint of water resistance, the powder component may be a hydrophobic powder component, such as titanium oxide, zinc oxide, talc, iron oxide, spherical polyalkyl acrylate, (meth)acrylic acid ester resin powder, polyamide resin powder (nylon powder), polyethylene powder, polystyrene powder, styrene (meth) acrylate copolymer resin powder, benzoguanamine resin powder, polytetrafluoroethylene powder, cellulose powder, polymethyl silsesquioxane powder, etc., as well as organo polysiloxane elastomer spherical powder or a composite spherical powder having organo polysiloxane elastomer spherical powder as a base powder.

In addition, a preferred embodiment of the water in oil type cosmetic of the present disclosure is characterized by the mass ratio of the compound which is solubilized by being neutralized and the water being greater than or equal to 0.02, from the viewpoint of preventing syneresis. There is a possibility that syneresis will occur if this mass ratio is less than 0.02.

Further, a preferred embodiment of the water in oil type cosmetic of the present disclosure is characterized by the mass ratio of the gelling agent and the powder component being less than or equal to 0.1, from the viewpoint of usability. If this mass ratio is greater than 0.1, there is a possibility that usability will deteriorate by the spreading properties of the cosmetic becoming poor and a refreshing sensation of use not being imparted.

Still further, a preferred embodiment of the water in oil type cosmetic of the present disclosure is characterized by further containing an emulsifying agent, from the viewpoint of preventing syneresis. The emulsifying agent is also not particularly limited. Examples of emulsifying agents include: silicone series surfactants, glycerin fatty acid ester, poly glycerin fatty acid ester, polyoxy ethylene glycerin fatty acid ester, sorbitan fatty acid ester, polyoxy ethylene sorbitan fatty acid ester, etc. Among these, a silicone series surfactant is preferable from the viewpoint of preventing syneresis.

The silicone series surfactant is not particularly limited as long as it is that which is capable of being employed in a water in oil type cosmetic. Examples of silicone series surfactants include: poly (oxyethylene/oxypropylene) methyl polysiloxane copolymer, polyoxy ethylene methyl polysiloxane copolymer, silicone chain branched methyl polysiloxane copolymer, alkyl chain branched polyoxy ethylene methyl polysiloxane copolymer, alkyl chain/silicone chain branched polyoxy ethylene methyl polysiloxane copolymer, crosslinked polyoxy ethylene methyl polysiloxane, alkyl group containing crosslinked polyoxy ethylene methyl polysiloxane, branched poly glycerin modified silicone, crosslinked poly glycerin modified silicone, alkyl group containing crosslinked poly glycerin modified silicone, and alkyl group branched poly glycerin modified silicone.

From the viewpoint of emulsification stability, preferred examples of the silicone series surfactant include: lauryl PEG-9 poly dimethyl siloxy ethyl dimethicone, PEG-9 poly dimethyl siloxy ethyl dimethicone, PEG-10 dimethicone, bisbutyl dimethicone polyglyceryl-3, cetyl PEG/PPG-10/1 dimethicone, PEG-12 dimethicone, dimethicone/(PEG-10/

15)) cross polymer, (dimethicone/polyglycerin-3) cross polymer, and (PEG-15/lauryl poly dimethyl siloxy ethyl dimethicone) cross polymer.

From the viewpoint of emulsification stability, these emulsifying agents may be blended in an amount within a range from 0.1 to 10% by mass with respect to the total amount of the water in oil cosmetic. This range is set because if the content of the emulsifying agent is less than 0.1% by mass, there is a possibility that syneresis cannot be prevented. Conversely, if the content of the emulsifying agent is greater than 10% by mass, there is a possibility that usability will deteriorate by the spreading properties of the cosmetic becoming poor and a refreshing sensation of use not being imparted.

The water in oil type cosmetic of the present disclosure may contain, within a range that will not adversely influence the object and the advantageous effects of the present disclosure, other components which are generally employed in cosmetics in addition to the components described above, as appropriate. Such other components include: water soluble polymers, oil soluble polymers, polymer powders, waxes, alcohols, liquid oils and fats, ester oils, hydrocarbon oils, silicone oils, fatty acids, higher order alcohols, fatty acid esters, pharmaceuticals, ultraviolet ray absorbing agents (other than those described above), ultraviolet scattering agents, etc.

Examples of water soluble polymers include: a homopolymer or a copolymer of 2-acrylamido-2-methyl propane sulfonic acid (hereinafter abbreviated as "AMPS"). The copolymer is a copolymer composed of comonomers such as vinyl pyrrolidone, acrylic acid amide, sodium acrylate and hydroxyethyl acrylate. That is, examples of the water soluble polymer include: AMPS homopolymer, vinyl pyrrolidone/AMPS copolymer, dimethyl acrylamide/AMPS copolymer, acrylic acid amide/AMPS copolymer, sodium acrylate/AMPS copolymer, etc.

Further examples of water soluble polymers include: carboxy vinyl polymer, ammonium poly acrylate, sodium poly acrylate, sodium acrylate/alkyl acrylate/sodium methacrylate/alkyl methacrylate copolymer, carrageenan, pectin, mannan, curdlan, chondroitin sulfate, starch, glycogen, arabic gum, sodium hyaluronate, tragacanth gum, xanthan gum, mucoitin sulfate, hydroxy ethyl guar gum, carboxy methyl guar gum, guar gum, dextran, kerato sulfate, locust bean gum, succinoglucan, chitin, chitosan, carboxy methyl chitin, agar, etc.

Trimethyl siloxy silicate is an example of an oil soluble polymer.

Examples of polymer powders include: dimethicone cross polymer, (dimethicone/vinyl dimethicone) cross polymer, polymethyl silsesquioxane, polyethylene, polymethyl methacrylate, etc.

Examples of waxes include: beeswax, candelilla wax, carnauba wax, lanolin, liquid lanolin, jojoba wax, etc.

Examples of alcohols include: lower order alcohols such as ethanol and isopropanol; higher order alcohols such as isostearyl alcohol, octyl dodecanol, hexyl decanol; and multivalent alcohols such as ethylene glycol, propylene glycol, 1, 3-butylene glycol, dipropylene glycol, and polybutylene glycol; etc.

Examples of liquid oils and fats include: avocado oil, camellia oil, turtle oil, macadamia nut oil, corn oil, mink oil, olive oil, rapeseed oil, egg yolk oil, sesame oil, persic oil, wheat germ oil, camellia sasanqua oil, castor oil, linseed oil, safflower oil, cottonseed oil, perilla seed oil, soybean oil, peanut oil, tea seed oil, kaya oil, rice bran oil, cinnamon oil, Japanese paulonia oil, jojoba oil, germ oil, triglycerin, etc.

Examples of ester oils include: isopropyl myristate, cetyl octanoate, octyl dodecyl myristate, isopropyl palmitate, butyl stearate, hexyl laurate, myristyl myristate, cetyl oleate, decyl oleate, hexyl decyl dimethyl octanoate, cetyl lactate, lactate myristyl, lanolin acetate, isocetyl stearate, isocetyl isostearate, isononyl isononanoate, cholesteryl 12-hydroxy stearate, ethylene glycol di-2-ethyl hexanoate, dipenta erythritol fatty acid ester, N-alkyl glycol monoisostearate, neopentyl glycol dicaprate, diisostearyl malate, glycerin di-2-heptylundecanoate, trimethylolpropane tri-2-ethyl hexanoate, trimethylolpropane triisostearate, penta erythritol tetra-2-ethyl hexanoate, glycerin tri-2-ethyl hexanoate, glycerin trioctanoate, glycerin triisopalmitate, trimethylolpropane triisostearate, cetyl 2-ethyl hexanoate, 2-ethyl hexyl palmitate, glycerin trimyristate, glyceride tri 2-heptylundecanoate, castor oil fatty acid methyl ester, oleyl oleate, acetoglyceride, 2-heptylundecyl palmitate, diisobutyl adipate, N-lauroyl-L-glutamate-2-octyl dodecyl ester, di-2-heptylundecyl adipate, ethyl laurate, di-2-ethyl hexyl sebacate, myristate 2-hexyl decyl, palmitate 2-hexyl decyl, 2-hexyl decyl adipate, diisopropyl sebacate, 2-ethyl hexyl succinate, triethyl citrate, etc.

Examples of hydrocarbon oils include liquid paraffin, ozokerite, squalane, pristane, paraffin, ceresin, squalene, petrolatum, microcrystalline wax, polyethylene wax, Fischer-Tropsch wax, etc.

Examples of silicone oils include: dimethyl polysiloxane, octamethyl siloxane, decamethyl tetrasiloxane, methyl hydrogen polysiloxane, methyl phenyl polysiloxane, hexamethyl cyclotrisiloxane, octamethyl cyclotetrasiloxane, decamethyl cyclopentasiloxane, etc.

Examples of fatty acids include laurate, myristate, palmitate, stearate, behenate, arachidonate, etc.

Examples of higher order alcohols include: lauryl alcohol, myristyl alcohol, cetyl alcohol, stearyl alcohol, behenyl alcohol, aralkyl alcohol, batyl alcohol, chimyl alcohol, carnerville alcohol, ceryl alcohol, colyanyl alcohol, myricyl alcohol, laxeryl alcohol, elaidyl alcohol, isostearyl. glyceryl ether, octyl alcohol, triacontyl alcohol, serachyl alcohol, cetostearyl alcohol, oleyl alcohol, lanolin alcohol, hydrogenated lanolin alcohol, hexyl decanol, octyl decanol, etc.

Examples of fatty acid esters include: myristyl myristate, cetyl palmitate, cholesteryl stearate, beeswax fatty acid 2-octyl dodecyl, etc.

Examples of pharmaceuticals include: L-ascorbic acid and derivative salts thereof; glycyrrhizinate and derivatives thereof, such as dicaryl glycyrrhizinate and mono ammonium glycyrrhizinate; glycyrrhetinate and derivatives thereof, such as stearyl glycyrrhetinate, allantoin; tranexamate and derivative salts thereof, alkoxy salicylate and derivative salts thereof; glutathione and derivative salts thereof, allantoin, azulene, etc.

Examples of other ultraviolet ray absorbing agents other than the ultraviolet ray absorbing agents described above include: cinnamate derivatives such as isopropyl methoxy cinnamate and isoamyl methoxy cinnamate; para-amino benzoate (hereinafter abbreviated as "PABA") derivatives such as ethyl PABA, ethyl-dihydroxy propyl PABA, ethyl hexyl-dimethyl PABA, glyceryl PABA; salicylate derivatives such as dipropylene glycol salicylate and TEA salicylate; benzophenone derivatives such as benzophenone-1, benzophenone-2, benzophenone-3 or oxybenzone, benzophenone-4, benzophenone-5, benzophenone-6, benzophenone-8, benzophenone-9, and benzophenone-12; benzylidene camphor derivatives such as 3-benzylidene camphor, 4-methyl benzylidene camphor, benzylidene camphor sulfonic acid, camphor benzalkonium methosulfate, terephthalylidene camphor sulfonic acid, and polyacrylamide methyl benzylidene camphor; triazine derivatives such as aniso triazine, ethyl hexyl triazone, diethyl hexyl butamido triazone, 2, 4, 6-tris (diisobutyl-4'-amino benzalmalonate)-s-triazine; phenyl benzimidazole derivatives such as phenyl dibenzimidazole tetra sulfonate disodium; phenyl benzo triazole derivatives such as drometrizole trisiloxane and methylene bis (benzo triazolyl tetra methyl butyl phenol); anthranyl derivatives such as menthyl anthranilate; imidazoline derivatives such as ethyl hexyl dimethoxy benzylidene dioxo imidazoline propyonate; benzalmalonate derivatives such as poly organosiloxane having a benzalmalonate functional group; 4,4-diaryl butadiene derivatives such as 1, 1-dicarboxy (2, 2'-dimethyl propyl)-4, 4-diphenyl butadiene, etc.

Examples of ultraviolet ray scattering agents include: inorganic pigments such as titanium dioxide which has undergone a hydrophobizing treatment, and zing oxide.

The water in oil type cosmetic of the present disclosure includes emulsified products and cream products. These products may be prepared by mixing the essential components described above and components which are generally added to cosmetics by a conventional method.

Hereinafter, an embodiment of the present disclosure will be described with reference to Examples. However, the present disclosure is not limited to the Examples. In addition, the contents of components which are blended in the Examples are indicated as percentages by mass, unless explicitly described otherwise.

Examples 1 Through 8 and Comparative Examples 1 and 2

First, the water in oil type cosmetic composition for preventing syneresis and the water in oil type cosmetic of the present disclosure were produced according to the preparations shown in Table 1, by a conventional method. First, components A and C, which are oil phases, were mixed and dissolved. Next, component B was added and dispersed. Further, component D, which is a powder component, was added. Then, component H, which was dissolved by component G neutralizing component F to become component E, was ultimately mixed and dissolved sufficiently uniformly, to produce single layer compositions and cosmetics. Note that components A through H are those which are shown in Table 1 below.

In Examples 1 through 8, phenyl benzimidazole sulfonate was employed as the compound which is solubilized by being neutralized, disteardimonium hectorite was employed as the gelling agent, titanium oxide, zinc oxide, talc, poly methyl silsesquioxane, methyl methacrylate cross polymer, and iron oxide were employed as the powder component, and experiments were conducted. Table 1 shows the results of an investigation regarding the syneresis preventing effects of the oil type cosmetic compositions for preventing syneresis and the water in oil type cosmetics for various examples of preparations.

TABLE 1

| | | Comparative Example 1 | Comparative Example 2 | Example 1 | Example 2 | Example 3 | Example 4 | Example 5 | Example 6 | Example 7 | Example 8 |
|---|---|---|---|---|---|---|---|---|---|---|---|
| A | Cyclopentasiloxane | 25.0 | 25.0 | 22.5 | 22.5 | 22.5 | 20.5 | 18.5 | 22.5 | 22.5 | 22.5 |
| | PEG-10 Dimethicone | 2.0 | 2.0 | 2.0 | 2.0 | 2.0 | 2.0 | 2.0 | 2.0 | 2.0 | 2.0 |
| | Lauryl PEG-9 Poly Dimethyl Siloxy Ethyl Dimethicone | 3.5 | 3.5 | 3.5 | 3.5 | 3.5 | 3.5 | 3.5 | 3.5 | 3.5 | 3.5 |
| | Cetyl Ethyl Hexanoate | 2.0 | 2.0 | 2.0 | 2.0 | 2.0 | 2.0 | 2.0 | 2.0 | 2.0 | 2.0 |
| | Disteardimmonium Chloride | 0.1 | 0.1 | 0.1 | 0.1 | 0.1 | 0.1 | 0.1 | 0.1 | 0.1 | 0.1 |
| | Dimethicone | 5.0 | 5.0 | 5.0 | 5.0 | 5.0 | 5.0 | 5.0 | 5.0 | 5.0 | 5.0 |
| | Isostearate | 1.0 | 1.0 | 1.0 | 1.0 | 1.0 | 1.0 | 1.0 | 1.0 | 1.0 | 1.0 |
| | Sesquiisostearate | 1.0 | 1.0 | 1.0 | 1.0 | 1.0 | 1.0 | 1.0 | 1.0 | 1.0 | 1.0 |
| | Sorbitan Palmitate | 0.1 | 0.1 | 0.1 | 0.1 | 0.1 | 0.1 | 0.1 | 0.1 | 0.1 | 0.1 |
| B | Disteardimmonium Hectorite | 1.0 | 1.0 | 1.0 | 1.0 | 1.0 | 1.0 | 1.0 | 0.6 | 0.8 | 1.5 |
| C | Dextrin Paimitate | 1.0 | 1.0 | 1.0 | 1.0 | 1.0 | 1.0 | 1.0 | 1.0 | 1.0 | 1.0 |
| D | Pigment Grade Titanium Oxide | 4.0 | 4.0 | 4.0 | 4.0 | 4.0 | 4.0 | 4.0 | 4.0 | 4.0 | 4.0 |
| | Fatty Acid Treated Titanium Oxide | 5.0 | | 5.0 | | | | | | 5.0 | 5.0 | |
| | Silica Coated Titanium Oxide | | 5.0 | | 5.0 | 5.0 | 5.0 | 5.0 | | | 5.0 |
| | Silicone Treated Zinc Oxide | 12.0 | 12.0 | 10.0 | 10.0 | 10.0 | 10.0 | 10.0 | 10.0 | 10.0 | 10.0 |

TABLE 1-continued

| | | Comparative Example 1 | Comparative Example 2 | Example 1 | Example 2 | Example 3 | Example 4 | Example 5 | Example 6 | Example 7 | Example 8 |
|---|---|---|---|---|---|---|---|---|---|---|---|
| | Talc | 1.0 | 1.0 | 1.0 | 1.0 | 1.0 | 1.0 | 1.0 | 1.0 | 1.0 | 1.0 |
| | Polymethyl Silsequioxane | 3.0 | 3.0 | 3.0 | 3.0 | 3.0 | 3.0 | 3.0 | 3.0 | 3.0 | 3.0 |
| | Methyl Methacrylate Cross Polymer | 3.0 | 3.0 | 3.0 | 3.0 | 3.0 | 3.0 | 3.0 | 3.0 | 3.0 | 3.0 |
| | Red Iron Oxide | 1.0 | 1.0 | 1.0 | 1.0 | 1.0 | 1.0 | 1.0 | 1.0 | 1.0 | 1.0 |
| | Yellow Iron Oxide | 2.0 | 2.0 | 2.0 | 2.0 | 2.0 | 2.0 | 2.0 | 2.0 | 2.0 | 2.0 |
| | Black Iron Oxide | 0.1 | 0.1 | 0.1 | 0.1 | 0.1 | 0.1 | 0.1 | 0.1 | 0.1 | 0.1 |
| E | Water | 20.3 | 20.3 | 23.6 | 23.3 | 22.4 | 24.4 | 26.4 | 21.7 | 21.5 | 20.3 |
| | Ethanol | 2.0 | 2.0 | 2.0 | 2.0 | 2.0 | 2.0 | 2.0 | 2.0 | 2.0 | 2.0 |
| | Phenoxy Ethanol | 0.5 | 0.5 | 0.5 | 0.5 | 0.5 | 0.5 | 0.5 | 0.5 | 0.5 | 0.5 |
| F | Phenyl Benzimidazole Sulfonate | | | 0.9 | 0.9 | 1.5 | 1.5 | 1.5 | 1.5 | 1.5 | 1.5 |
| G | AMPD | | | 0.3 | | | | | 1.0 | 1.0 | |
| | TEA | | | 0.0 | 0.6 | 0.9 | 0.9 | 0.9 | 1.0 | 1.0 | 2.5 |
| | EDTA-3Na | 0.2 | 0.2 | 0.2 | 0.2 | 0.2 | 0.2 | 0.2 | 0.2 | 0.2 | 0.2 |
| H | Citric Acid | 0.0 | 0.0 | 0.0 | 0.0 | 0.0 | 0.0 | 0.0 | 0.0 | 0.0 | 0.0 |
| | Sodium Citrate | 0.2 | 0.2 | 0.2 | 0.2 | 0.2 | 0.2 | 0.2 | 0.2 | 0.2 | 0.2 |
| | Glycerin | 4.0 | 4.0 | 4.0 | 4.0 | 4.0 | 4.0 | 4.0 | 4.0 | 4.0 | 4.0 |
| | | 100.0 | 100.0 | 100.0 | 100.0 | 100.0 | 100.0 | 100.0 | 100.0 | 100.0 | 100.0 |
| | Usability | ○ | ○ | ○ | ○ | ○ | ○ | ○ | ○ | ○ | ○ |
| | Stability | * | X | ○ | ○ | ○ | ○ | ○ | ○ | ○ | ○ |
| | Sulfonic Acid/Water | 0 | 0 | 0.038136 | 0.038627 | 0.066964 | 0.061475 | 0.056818 | 0.069061 | 0.069703 | 0.073892 |
| | Bentone/Powder | 0.032154 | 0.032154 | 0.034364 | 0.034364 | 0.034364 | 0.034364 | 0.034364 | 0.020619 | 0.027491 | 0.051546 |
| | Viscosity (mPa · s) | 42000 | 37000 | 42000 | 42000 | 42000 | 42000 | 42000 | 38000 | 38000 | 50000 |

<Usability>

The cosmetics were applied to the faces of a panel of ten experts, and the ease of spreading on the skin and the refreshing sensation imparted by the cosmetics were evaluated. Evaluations were conducted according to the following standards and are indicated as symbols in the table.

Evaluations

O: Greater than or equal to seven among the ten panel members evaluated the cosmetics as being easy to spread and imparted a refreshing sensation.

X: Less than or equal to six among the ten panel members evaluated the cosmetics as being easy to spread and imparted a refreshing sensation.

<Stability>

Stability was evaluated by forming uniform single layers, statically storing the cosmetics for one month at 50° C., and observing whether syneresis occurred. The conditions of static storage were as follows. 30 g of the cosmetics were placed in a laminated tube container having polyethylene as a principal material and an opening diameter φ of 25 mm. The tube containers were inverted, and whether a transparent oil layer formed at the upper portion was confirmed.

In addition, in the Examples below, the following measuring device and measuring conditions were employed to measure the viscosity of the composition or the cosmetic.
Measuring Device: Shibaura System Co., Ltd. B type Viscometer Model Number VDA2
Measurement conditions: 12 rpm, 1 minute, 30° C.

It was found from the results of Table 1 that all of Examples 1 through 8 of the water in oil type cosmetic composition for preventing syneresis and the water in oil type cosmetic of the present disclosure exhibited favorable syneresis preventing effects as well as favorable spreading properties.

In contrast, syneresis occurred in the cosmetics of Comparative Examples 1 and 2 after two weeks of static storage at 50° C. following production thereof. That is, Comparative Examples 1 and 2 were unstable.

Examples 9 Through 11 and Comparative Examples 3 and 4

Next, the water in oil type cosmetic composition for preventing syneresis and the water in oil type cosmetic of the present disclosure were produced according to the preparations shown in Tablet, by a conventional method, with the same procedures as those which were employed to produce Example 1, etc.

In Examples 9 through 11, phenyl benzimidazole sulfonate, terephthalylidene dicamphor sulfonate, and (acryloyl dimethyl taurine ammonium/VP) copolymer were employed as the compound which is solubilized by being neutralized, disteardimonium hectorite was employed as the gelling agent, titanium oxide, zinc oxide, talc, poly methyl silsesquioxane, methyl methacrylate cross polymer, and iron oxide were employed as the powder component, and experiments were conducted. Table 2 shows the results of an investigation regarding the syneresis preventing effects of the oil type cosmetic compositions for preventing syneresis and the water in oil type cosmetics for various examples of preparations.

TABLE 2

| | Comparative Example 3 | Comparative Example 4 | Example 9 | Example 10 | Example 11 |
|---|---|---|---|---|---|
| Ethyl Hexyl Methoxy Cinnamate | 7.5 | 7.5 | 7.5 | 7.5 | 7.5 |
| Dimethicone | 3.0 | 4.0 | 4.0 | 3.9 | 3.9 |
| Cyclopentasiloxane | 12.5 | 10.0 | 10.0 | 10.0 | 10.0 |
| Trimethyl Siloxy Silicate | 1.0 | 1.0 | 1.0 | 1.0 | 1.0 |
| PEG-10 Dimethicone | 3.0 | 3.8 | 3.8 | 3.8 | 3.8 |
| Polybutyrene Glycol | 2.0 | 2.0 | 2.0 | 2.0 | 2.0 |
| Isostearate | 0.1 | 0.4 | 0.4 | 0.4 | 0.4 |
| Lauryl PEG-9 Poly Dimethyl Siloxy Ethyl Dimethicone | | 2.0 | 2.0 | 2.0 | 2.0 |
| Cyclopentasiloxane | 5.0 | 5.0 | 5.0 | 5.0 | 5.0 |
| Disteardimonium Hectorite | 0.8 | 1.0 | 1.0 | 1.0 | 1.0 |
| Fatty Acid Treated Titanium Oxide | 7.0 | 7.0 | 7.0 | 7.0 | 7.0 |
| Pigment Grade Titanium Oxide | 2.0 | 2.0 | 2.0 | 2.0 | 2.0 |
| Talc | 2.0 | 2.0 | 2.0 | 2.0 | 2.0 |
| Polymethyl Silsesquioxane | 2.0 | 2.0 | 2.0 | 2.0 | 2.0 |
| Methyl Methacrylate Cross Polymer | 4.0 | 4.0 | 4.0 | 4.0 | 4.0 |
| Silica | 1.0 | 1.0 | 1.0 | 1.0 | 1.0 |
| Mica | 0.5 | 0.5 | 0.5 | 0.5 | 0.5 |
| Red Iron Oxide | 0.4 | 0.4 | 0.4 | 0.4 | 0.4 |
| Yellow Iron Oxide | 1.2 | 1.2 | 1.2 | 1.2 | 1.2 |
| Water | 35.3 | 33.5 | 31.9 | 32.0 | 33.1 |
| EDTA-3Na | 0.2 | 0.2 | 0.2 | 0.2 | 0.2 |
| Phenyl Benzimidazole Sulfonate | | | 1.0 | | |
| Terephthalylidene Dicamphor Sulfonate | | | | 1.0 | |
| (Acryloyl Dimethyl Taurine Ammonium/VP) Copolymer | | | | | 0.5 |
| TEA | | | 0.6 | 0.6 | |
| Glycerin | 4.0 | 4.0 | 4.0 | 4.0 | 4.0 |
| Ethanol | 5.0 | 5.0 | 5.0 | 5.0 | 5.0 |
| Phenoxy Ethanol | 0.5 | 0.5 | 0.5 | 0.5 | 0.5 |
| Total | 100.0 | 100.0 | 100.0 | 100.0 | 100.0 |
| Usability | ○ | ○ | ○ | ○ | ○ |
| Stability | X | X | ○ | ○ | Δ |
| Sulfonic Acid/Water | 0 | 0 | 0.031348 | 0.031250 | 0.015106 |
| Bentone/Powder | 0.039801 | 0.049751 | 0.049751 | 0.049751 | 0.049751 |
| Viscosity (mPa · s) | 25000 | 24000 | 30000 | 30000 | 30000 |

<Usability>

The cosmetics were applied to the faces of a panel of ten experts, and the ease of spreading on the skin and the refreshing sensation imparted by the cosmetics were evaluated. Evaluations were conducted according to the following standards and are indicated as symbols in the table.

Evaluations

O: Greater than or equal to seven among the ten panel members evaluated the cosmetics as being easy to spread and imparted a refreshing sensation.

X: Less than or equal to six among the ten panel members evaluated the cosmetics as being easy to spread and imparted a refreshing sensation.

<Stability>

Stability was evaluated by forming uniform single layers, statically storing the cosmetics for one month at 50° C., and observing whether syneresis occurred. The conditions of static storage were as follows. 30 g of the cosmetics were placed in a laminated tube container having polyethylene as a principal material and an opening diameter φ of 25 mm. The tube containers were inverted, and whether a transparent oil layer formed at the upper portion was confirmed.

It was found from the results of Table 2 that all of Examples 9 through 11 of the water in oil type cosmetic composition for preventing syneresis and the water in oil type cosmetic of the present disclosure exhibited favorable syneresis preventing effects as well as favorable spreading properties.

In contrast, syneresis occurred in the cosmetics of Comparative Examples 3 and 4 after two weeks of static storage at 50° C. following production thereof. That is, Comparative Examples 3 and 4 were unstable.

Example 12 and Comparative Example 5

In Example 12, phenyl benzimidazole sulfonate was employed as the compound which is solubilized by being neutralized, disteardimonium hectorite was employed as the gelling agent, titanium oxide and methyl methacrylate cross polymer were employed as the powder component, and experiments were conducted. Table 3 shows the results of an investigation regarding the syneresis preventing effects of the oil type cosmetic compositions for preventing syneresis and the water in oil type cosmetics for various examples of preparations.

TABLE 3

|  | Example 12 | Comparative Example 5 |
|---|---|---|
| Lauryl PEG-9 Poly Dimethyl Siloxy Ethyl Dimethicone | 3 | 3 |
| Disteardimonium Hectorite | 1 | 1 |
| Cyclopentasiloxane | 27 | 31 |
| Trimethyl Siloxy Silicate | 1 | 1 |
| Isostearate | 0.5 | 0.5 |
| Ethyl Hexyl Methoxy Cinnamate | 4 | 4 |
| Fatty Acid Treated Titanium Oxide | 7 | 7 |
| Methyl Methacrylate Cross Polymer | 5 | 5 |
| Pigment Grade Titanium Oxide | 1 | 1 |
| Water | 39.09 | 35.09 |
| Phenyl Benzimidazole Sulfonate | 1.5 | 1.5 |
| Ethanol | 0.5 | 0.5 |
| DPG | 5 | 5 |
| BG | 2.5 | 2.5 |
| Citric Acid | 0.01 | 0.01 |
| Sodium Citrate | 0.1 | 0.1 |
| TEA | 0.9 | 0.9 |
| Phenoxy Ethanol | 0.5 | 0.5 |
| Methyl Paraben | 0.2 | 0.2 |
| EDTA-3Na | 0.2 | 0.2 |
| Usability | ○ | ○ |
| Stability | ○ | X |
| Sulfonic Acid/Water | 0.038373 | 0.041563 |
| Bentone/Powder | 0.076923 | 0.076923 |
| Viscosity (mPa·s) | 13000 | 6500 |

<Usability>

The cosmetics were applied to the faces of a panel of ten experts, and the ease of spreading on the skin and the refreshing sensation imparted by the cosmetics were evaluated. Evaluations were conducted according to the following standards and are indicated as symbols in the table.

Evaluations

O: Greater than or equal to seven among the ten panel members evaluated the cosmetics as being easy to spread and imparted a refreshing sensation.

X: Less than or equal to six among the ten panel members evaluated the cosmetics as being easy to spread and imparted a refreshing sensation.

<Stability>

Stability was evaluated by forming uniform single layers, statically storing the cosmetics for one month at 50° C., and observing whether syneresis occurred. The conditions of static storage were as follows. 30 g of the cosmetics were placed in a laminated tube container having polyethylene as a principal material and an opening diameter φ of 25 mm. The tube containers were inverted, and whether a transparent oil layer formed at the upper portion was confirmed.

It was found from the results of Table 3 that Example 12 of the water in oil type cosmetic composition for preventing syneresis and the water in oil type cosmetic of the present disclosure exhibited favorable syneresis preventing effects as well as favorable spreading properties.

In contrast, syneresis occurred in the cosmetic of Comparative Example 5 24 hours after production thereof. That is, Comparative Example 5 was unstable. In addition, 24 hours after Comparative Example 5 was shaken ten times under RT, a transparent layer appeared at the upper portion thereof, and it became clear that a uniform single layer cannot be formed as by the present disclosure.

In addition, a water soluble ultraviolet ray absorbing agent may be utilized as the compound which is solubilized by being neutralized in the present disclosure as described above. Therefore, the present disclosure may be utilized as a sunscreen cosmetic which is capable of preventing syneresis.

The invention claimed is:

1. A water in oil cosmetic, comprising:
   a compound which is solubilized by being neutralized;
   a gelling agent;
   water; and
   a powder component;
   the viscosity of the water in oil cosmetic being greater than or equal to 30000 mPa·s, wherein
   the compound which is solubilized by being neutralized is at least one selected from a group consisting of phenyl benzimidazole sulfonic acid, terephthalylidene dicamphor sulfonic acid and an ammonium acryloyldimethyltaurate/VP copolymer, and is blended in an amount within a range from 0.01 to 5% by mass, based on the total amount of the water in oil cosmetic, and
   the mass ratio of the compound which is solubilized by being neutralized with respect to the water is greater than or equal to 0.02.

2. The water in oil cosmetic as defined in claim 1, wherein:
   the mass ratio of the gelling agent with respect to the powder component is less than or equal to 0.1.

3. The water in oil cosmetic as defined in claim 1, further comprising:
   an emulsifying agent.

4. The water in oil cosmetic as defined in claim 1, wherein:
   the gelling agent is a clay mineral.

5. The water in oil cosmetic as defined in claim 4, wherein:
   the clay mineral is an organically modified clay mineral.

6. The water in oil cosmetic as defined in claim 3, wherein:
   the emulsifying agent is a silicone surfactant.

* * * * *